(12) United States Patent
Loh et al.

(10) Patent No.: US 12,343,112 B2
(45) Date of Patent: *Jul. 1, 2025

(54) DEVICE AND METHOD FOR DIAGNOSING VESSEL OCCLUSION

(71) Applicant: Loh Medical Holdings LLC, Seattle, WA (US)

(72) Inventors: Yince Loh, Seattle, WA (US); Kendall S Hartung, Carnation, WA (US); Leo C Bolero, Brisbane (AU); Michael E Baum, Bellevue, WA (US); David H Gusdorf, Cle Elum, WA (US)

(73) Assignee: Loh Medical Holdings, LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/674,505

(22) Filed: May 24, 2024

(65) Prior Publication Data

US 2024/0306915 A1   Sep. 19, 2024

Related U.S. Application Data

(60) Continuation of application No. 18/423,744, filed on Jan. 26, 2024, which is a continuation-in-part of
(Continued)

(51) Int. Cl.
| | |
|---|---|
| *A61B 5/00* | (2006.01) |
| *A61B 5/026* | (2006.01) |
| *A61B 8/00* | (2006.01) |
| *A61B 8/06* | (2006.01) |
| *A61B 8/08* | (2006.01) |

(52) U.S. Cl.
CPC .......... *A61B 5/0042* (2013.01); *A61B 5/0261* (2013.01); *A61B 5/6803* (2013.01); *A61B 5/7282* (2013.01); *A61B 8/06* (2013.01); *A61B 8/0891* (2013.01); *A61B 8/4209* (2013.01); *A61B 8/4227* (2013.01); *A61B 8/5223* (2013.01); *A61B 5/684* (2013.01); *A61B 8/4254* (2013.01); *A61B 8/488* (2013.01); *A61B 2576/026* (2013.01)

(58) Field of Classification Search
None
See application file for complete search history.

(56) References Cited

U.S. PATENT DOCUMENTS

| | | | |
|---|---|---|---|
| 2008/0132790 A1* | 6/2008 | Burton | A61B 8/0833 600/447 |
| 2013/0072804 A1* | 3/2013 | Inoue | A61B 5/4064 600/476 |

(Continued)

*Primary Examiner* — Jonathan Cwern
(74) *Attorney, Agent, or Firm* — LeFevour Law, LLC; Martin LeFevour

(57) ABSTRACT

A portable device for detecting a large vessel occlusion in a patient's brain by transmitting a signal into both sides of the brain and receiving the reflections of the transmitted signals to capture a single reflection data point of the characteristics of the blood vessels and brain tissue on both sides of the brain. Using the captured single reflection data point values to perform a comparative analysis between the right and left side of the brain, and based on this analysis, assessing whether the patient is experiencing a large vessel occlusion. If so, the device generates an alert.

20 Claims, 9 Drawing Sheets

Related U.S. Application Data application No. 16/685,985, filed on Nov. 15, 2019, now abandoned, which is a division of application No. 15/828,840, filed on Dec. 1, 2017, now abandoned.

(60) Provisional application No. 62/517,549, filed on Jun. 9, 2017, provisional application No. 62/486,177, filed on Apr. 17, 2017.

(56) References Cited

U.S. PATENT DOCUMENTS

| | | | | |
|---|---|---|---|---|
| 2014/0347265 A1* | 11/2014 | Aimone | ................ | H04W 4/30 |
| | | | | 345/156 |
| 2017/0127946 A1* | 5/2017 | Levinson | ............... | G16H 50/20 |
| 2020/0054267 A1* | 2/2020 | Srinivasan | ........... | A61B 5/0261 |

* cited by examiner

DEVICE AND METHOD FOR DIAGNOSING VESSEL OCCLUSION

REFERENCE TO RELATED APPLICATIONS

This application is a continuation of application U.S. Ser. No. 18/423,744 filed on Jan. 26, 2024, which is a continuation-in-part application of U.S. Ser. No. 16/685,985 filed on Nov. 15, 2019, which is a division application of U.S. Ser. No. 15/828,840 filed on Dec. 1, 2017, which claims priority to U.S. Provisional Patent Application Ser. No. 62/486,177 filed Apr. 17, 2017, and to U.S. Provisional Patent Application Ser. No. 62/517,549 filed Jun. 9, 2017; the disclosures of each application which are incorporated herein in their entirety.

BACKGROUND

Nearly 800,000 strokes occur in the U.S. annually, and almost 3 million Americans are currently disabled from them. Stroke is the third leading cause of death in the U.S. and is the leading cause of disability costing over $73 billion/year in the U.S. alone.

The most disabling and deadly ischemic strokes (i.e., lack of blood flow to the brain) result from large vessel occlusions ("LVO"). Patients with LVO's have extremely poor outcomes without treatment. Developments over the years have shown that LVO's in brain vessels can be extracted using devices and catheters inserted through the groin artery. Studies, during this same timeframe, showed a positive benefit of endovascular therapy ("EVT") over prior medical management of LVO's, and several of these studies showed that earlier intervention produced better clinical outcomes.

In one study, patients transferred to a hospital without EVT capability had an average delay of two hours before arriving to the final EVT-capable facility. This is an unacceptable delay when time is critical to preserving brain function. The emerging dilemma lies in accurate field stroke triage. Only a portion of ischemic strokes result from LVO's, and EVT does not benefit the rest. Movement of both LVO and non-LVO stroke patients to a single EVT-capable center might delay or deprive a patient of standard of care treatment for non-LVO strokes. It might also overwhelm an EVT-capable hospital.

Imaging identification of LVO's exists with MRI and CT, but these methods, due to the size of the equipment involved and the calculations being made, typically require a trained operator in a hospital environment and are not suitable for use in a field environment. Attempts to create portable, field useable devices that detect LVO's are still not ideal. These devices, typically, are fairly complex and measure cerebral oximetry; requiring substantial calculation power and hardware to perform intricate calculations. Further, cerebral oximetry alone is known to be a highly inaccurate estimator of true oxygen saturation of the brain because of differences in patient skin color, skull thickness, among other things. Its main utilization is to trend a specific person's cerebral oximetry values. In other words, the patient's cerebral oximetry value, at one time (preferably during the normal state), is used as a basis of longitudinal comparison when said patient is anticipated to be placed under physiological stress, such as prolonged cardiac arrest, cardiac surgery and cardiopulmonary bypass, or significant brain injury. Also, the sensors on an LVO detection device need to be placed in specific spots on the head to get proper readings. These other devices, to get them placed in the correct spot on the patient, require a highly trained operator who is trained in the proper placement of the LVO detection device. It is not feasible to have enough highly trained operators like this in the field, ready to respond to every emergency situation involving an LVO. These other LVO detection devices also, typically, take measurements for LVO's in areas of the brain which are not ideal, and often unreliable, for detecting an LVO.

Other devices measure cerebral oxygen, cerebral blood flow or cerebral oxygen saturation dynamically over time, such as over a cardiac cycle or any physiological time period. These devices first measure the amount of near-infrared and infrared light reflection, which are unique aspects of deoxyhemoglobin and oxyhemoglobin. Oxyhemoglobin and deoxyhemoglobin reflect light at different wavelengths. Different wavelength reflections are used to calculate the concentrations of both of these blood cell products. In these conventional cerebral oximetry devices, the signal from the photodiode is used to calculate oxyhemoglobin and deoxyhemoglobin concentrations. These values are then input into known physiological formulas to calculate the cerebral oxygen saturation level and cerebral blood flow within the tissue. Sometimes, these other devices implement a large band of sensors on both sides of the head to make their measurements, which can make readings unreliable since they are measuring through hair at some points, and they also sometimes use a compression mechanism to conduct a coherence test. These features of the other devices make them undesirable or inadequate for LVO detection in the field in an emergency situation because the features of these other devices create significant detection variability; often result in the sensors being placed in the incorrect position; often provide data that is unreliable or of little value in the field; require the device to be a bulky and fragile device and rely on complicated calculations and formulas to make an LVO assessment.

Accordingly, there is a need to diagnose LVOs quickly and provide appropriate medical intervention. The ideal adjunct to the EMT or paramedic assessing a possible stroke patient is a field-expedient, operator-independent device to help determine whether a patient, potentially needs EVT. Such a device could effectively diagnose while minimizing diagnostic error and operator training. Such a device could also help emergency doctors at non-EVT hospitals identify EVT-eligible patients earlier and expedite transfer to EVT-capable hospitals without doing additional time-consuming imaging.

SUMMARY

According to one aspect of the present invention, a portable head-mounted diagnostic device for diagnosing conditions consistent with the existence of a blockage of a blood vessel in the brain of a patient, such as a large vessel occlusion, may include a control assembly storing a threshold value; a pair of signal generation devices; a pair of reflected signal sensors; where the pair of signal generator devices each has the capability to transmit a signal into the brain of the patient, creating a reflected signal, and one of the pair of signal generation devices transmits a signal into the left side of the brain of the patient and the other of the pair of signal generation devices transmits a signal into the right side of the brain of the patient; where the pair of reflected signal sensors each has the capability to receive the created reflected signals and one of the pair of reflected signal sensors receives the reflected signal on the left side of the brain of the patient, and the other of the pair of reflected signal sensors receives the reflected signal on the right side of the brain of the patient; where the reflected signal sensors convert the received signals into a single data point amplitude value for each of the left side and right side of the brain; and where the control assembly calculates the difference between the single data point amplitude value for the left side of the brain and the single data point amplitude value for the right side of the brain and compares the calculated difference to the threshold value to determine if a large vessel occlusion condition exists.

According to another aspect of the present invention, a portable head-mounted diagnostic device for diagnosing conditions consistent with the existence of a blockage of a blood vessel in the brain of a patient, such as a large vessel occlusion, includes a control assembly storing a threshold value; a sensor support structure having a pair of signal generation devices, a pair of shallow reflected signal sensors; and a pair of deep reflected signal sensors; and a head engagement assembly having a temple arm structure and a connected pair of nose supports. The pair of signal generator devices each has the capability to transmit a signal into the brain of the patient, creating a shallow reflected signal and a deep reflected signal, and one of the pair of signal generation devices transmits a signal into the left side of the brain of the patient and the other of the pair of signal generation devices transmits a signal into the right side of the brain of the patient. The pair of shallow reflected signal sensors each has the capability to receive the created shallow reflected signals and one of the pair of shallow reflected signal sensors receives the shallow reflected signal on the left side of the brain of the patient, and the other of the pair of shallow reflected signal sensors receives the shallow reflected signal on the right side of the brain of the patient. Further, the pair of deep reflected signal sensors each has the capability to receive the created deep reflected signals and one of the pair of deep reflected signal sensors receives the deep reflected signal on the left side of the brain of the patient, and the other of the pair of deep reflected signal sensors receives the deep reflected signal on the right side of the brain of the patient.

The shallow reflected signal sensors and the deep reflected signal sensors, in this aspect of the invention, convert the received signals into a single data point amplitude value for each of the left side and right side of the brain. The control assembly calculates the difference between the single data point amplitude value for the left side of the brain and the single data point amplitude value for the right side of the brain for the shallow reflected signal and compares the calculated difference to the threshold value to determine if a large vessel occlusion condition exists; and calculates the difference between the single data point amplitude value for the left side of the brain and the single data point amplitude value for the right side of the brain for the deep reflected signal and compares the calculated difference to the threshold value to determine if a large vessel occlusion condition exists.

According to yet another aspect of the present invention, a method for diagnosing conditions consistent with the existence of a blockage of a blood vessel in the brain of a patient, such as a large vessel occlusion, includes the steps of providing a portable head-mounted diagnostic device having a control assembly storing a threshold value; a pair of signal generation devices and at least a pair of reflected signal sensors; transmitting a signal into the left side of the brain of the patient from one of the pair of signal generator devices, wherein the signal interaction with the blood vessels on the left side of the brain creates a reflected signal; simultaneously transmitting a signal into the right side of the brain of the patient from the other of the pair of signal generator devices, wherein the signal interaction with the blood vessels on the right side of the brain creates a reflected signal; receiving and converting the left side reflected signal into a single data point amplitude value at one of the pair of reflected signal sensors; receiving and converting the right side reflected signal into a single data point amplitude value at the other of the pair of reflected signal sensors; calculating the difference between the single data point amplitude value for the left side of the brain and the single data point amplitude value for the right side of the brain; and comparing the calculated difference to the threshold value to determine if a large vessel occlusion condition exists.

DRAWINGS

Objects, features, and advantages of the present invention will become apparent upon reading the following description in conjunction with the drawing figures, in which.

DESCRIPTION

Figure 1:
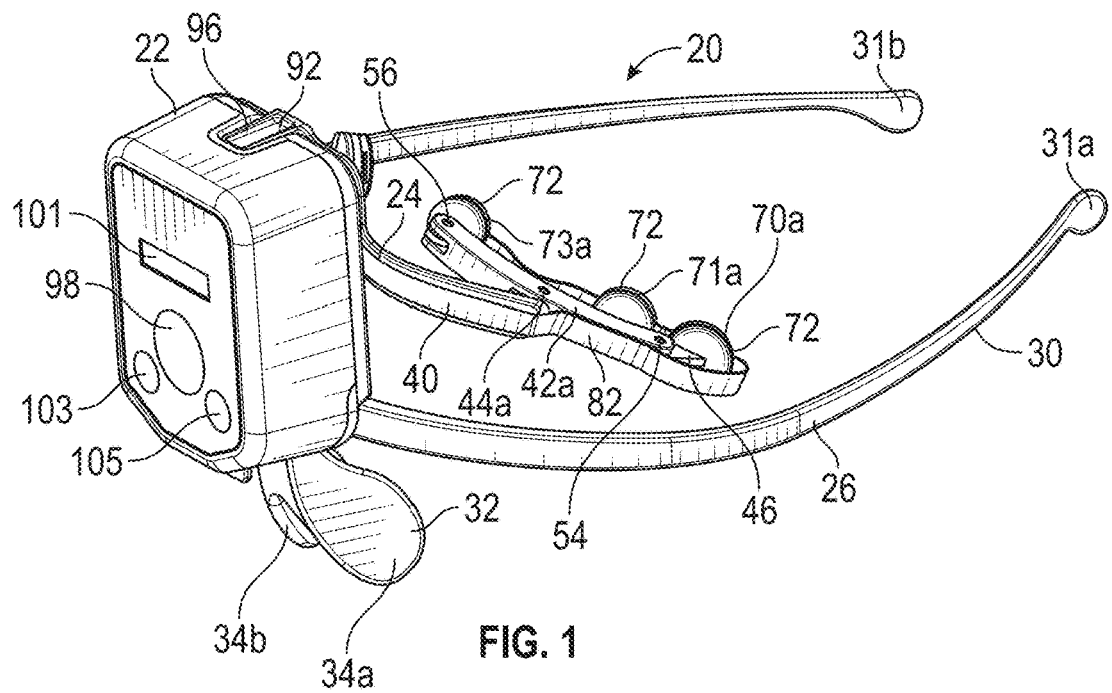
FIG. 1 is a front perspective view of an embodiment of an LVO detector assembly of the present invention.
Figure 2:
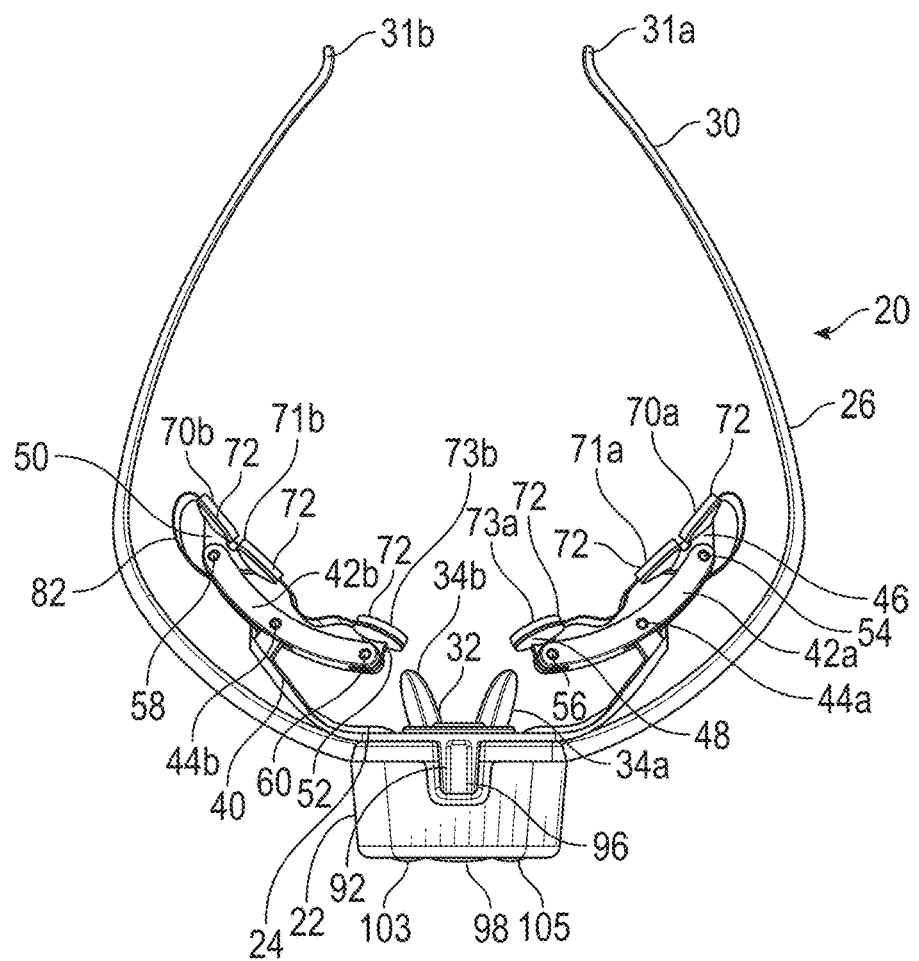
FIG. 2 is a top view of an embodiment of an LVO detector assembly of the present invention.
Figure 3:
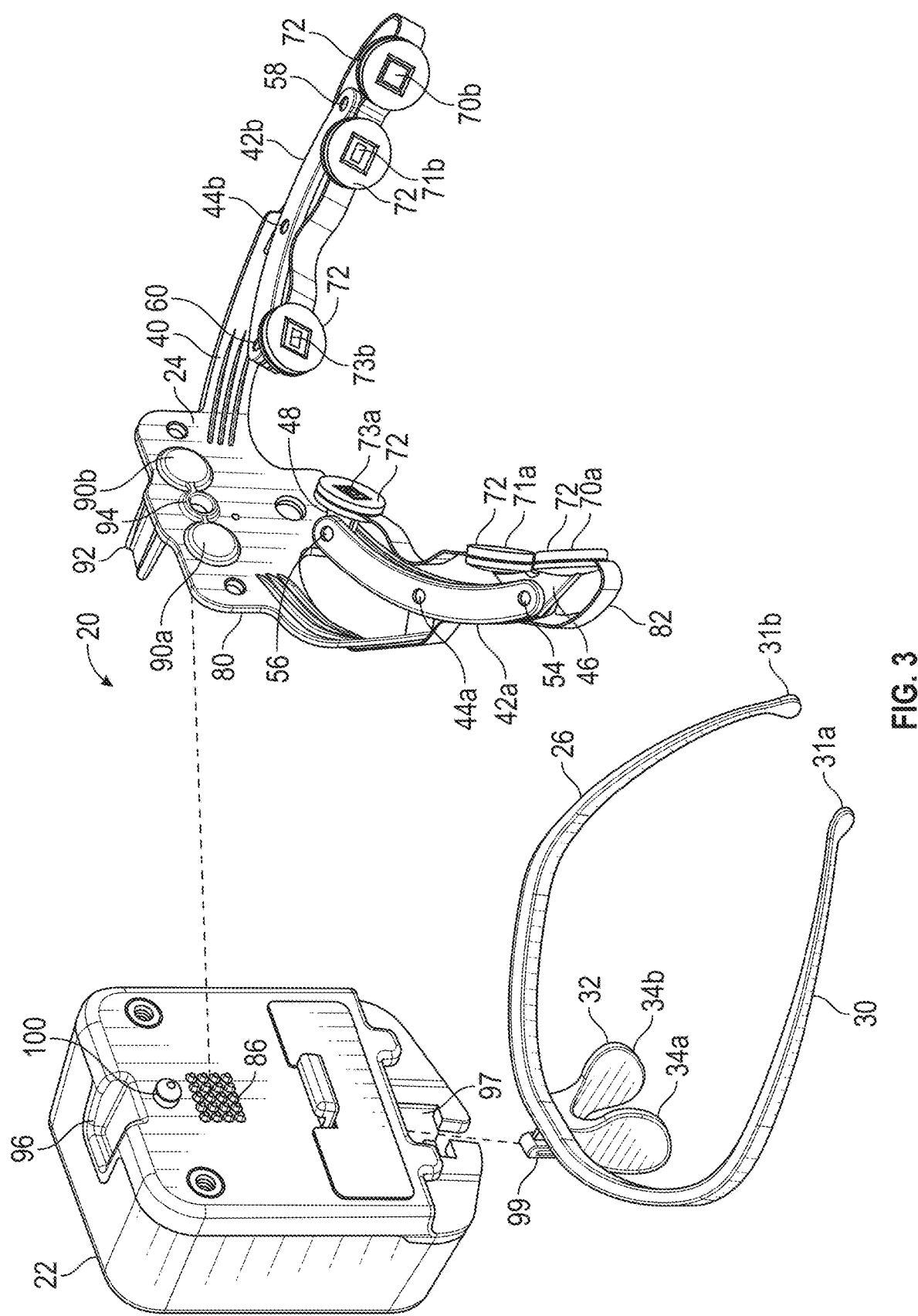
FIG. 3 is an exploded view of an embodiment of an LVO detector assembly of the present invention.

Referring to FIGS. 1-3, an embodiment of an LVO detector assembly 20 of the present invention is depicted. The LVO detector assembly 20 of the embodiment depicted includes the following components: a control assembly 22, a sensor support structure 24 and a head engagement assembly 26. The head engagement assembly 26, in this embodiment, includes a curved unified temple arm structure 30, which includes temple arm ends 31a, 31b, and a nose support structure 32 which includes nose pads 34a, 34b. The sensor support structure 24, in this embodiment, includes a main support arm 40, a pair of secondary support arms 42a, 42b connected to the main support arm 40 by hinged connectors 44a, 44b, respectively. Connected to the secondary support arm 42a, in this embodiment, is a first component support 46 and a second component support arm 48. The first component support 46 and the second component support 48 are connected to the first secondary support arm 42*a* by hinged connectors 54, 56, respectively. Similarly, connected to secondary support arm 42*b* is a third component support 50 and a fourth component support 52. The third component support 50 and the fourth component support 52 are connected to the secondary support arm 42*b* by hinged connectors 58, 60, respectively.

In this embodiment, the first and third component supports 46, 50 each have signal generation devices 70*a*, 70*b* (general reference to a signal generation device is designated as 70) and sensors 71*a*, 71*b* (general reference to a sensor is designated as 71 or 73) attached to them. In this embodiment, the signal generation devices 70*a*, 70*b* are infrared or near infrared light emitting diodes ("LED's"). It should be understood that in other embodiments of the present invention any number of signal generation devices 70 may be used; that the signal generation devices 70 may operate in any spectrum required and that the signal generation devices 70 may be set at any strength of signal required.

In this embodiment, the second and fourth supports 48, 52 each have sensors 73*a*, 73*b* attached to them. In this embodiment, the sensors 71*a*, 71*b*, 73*a*, 73*b* are photodiodes that receive and convert reflected infrared or near infrared signals generated by the LED's 70*a*, 70*b*. It should be understood that in other embodiments of the present invention any number of sensors 71, 73 may be used and that the sensors 71, 73 may receive energy in any spectrum or manner required. In this embodiment, each signal generation device 70*a*, 70*b* and sensor 71*a*, 71*b*, 73*a*, 73*b* is surrounded by a pad 72 attached to the corresponding first component support 46, second component support 48, third component support 50 or fourth component support 52. The pads 72 provide comfort to a patient and acts to help block unwanted ambient light from interfering with the signal generation devices 70*a*, 70*b* and the sensors 71*a*, 71*b*, 73*a*, 73*b*.

Further, the sensor support structure 40 is in power and command communication with the control assembly 22. Embedded on the sensor support structure 40 are a series of wires 82 that are integrated with and run through the sensor support structure 40 and ultimately connect with each signal generation device 70*a*, 70*b* and sensor 71*a*, 71*b*, 73*a*, 73*b* to power and provide command instructions from the control assembly 22 to each signal generation device 70*a*, 70*b* and sensor 71*a*, 71*b*, 73*a*, 73*b*.

In one embodiment, the components 22, 24, 26 of the LVO detector assembly 20 are integrated with one another in an inseparable configuration. In other embodiments, such as depicted in FIG. 3, the control assembly 22, the sensor support structure 24 and the head engagement assembly 26 may be separable from one another. In the medical environment in which the LVO detector assembly 20 is utilized, having separable components 22, 24, 26 has the advantage of being able to disconnect the sensor support structure 24 and the head engagement assembly 26 from the control assembly 22. This is advantageous because the lower cost components that interact with the patient (i.e., the sensor support structure 24 and the head engagement assembly 26) may be single-use components that are disposed of after each use, and the more expensive control assembly 22 can be re-used with other patients by connecting a new sensor support structure 24 and a new head engagement assembly 26. Disconnectable components 22, 24, 26 also provide the advantage that if differing or updated signal generation devices 70 or sensors 71, 73 need to be used or the sensor support structure 24 or the head engagement assembly 26 needs to be modified (e.g. different size, shape or material), then a different sensor support structure 24 or head engagement assembly 26 containing the modifications or updated structure may be connected to the control assembly 22. Further, in the disconnectable component embodiment, the sensor support structure 40 has a power and control interface 80 embedded on the sensor support structure 40. The power and control interface 80 connects with the series of wires 82. In this embodiment, the sensor support structure 24 also includes a pair of embedded magnets 90*a*, 90*b*, a protruding connection piece 92 and an alignment slot 94. In this embodiment, the control assembly 22 also has a power and control interface 86; a top connection slot 96; a bottom connection slot 97; an alignment post 100; an LVO alert screen 101; a power button 98 and control buttons 103, 105. The head engagement assembly 26 further has a connection tab 99.

Figure 4:
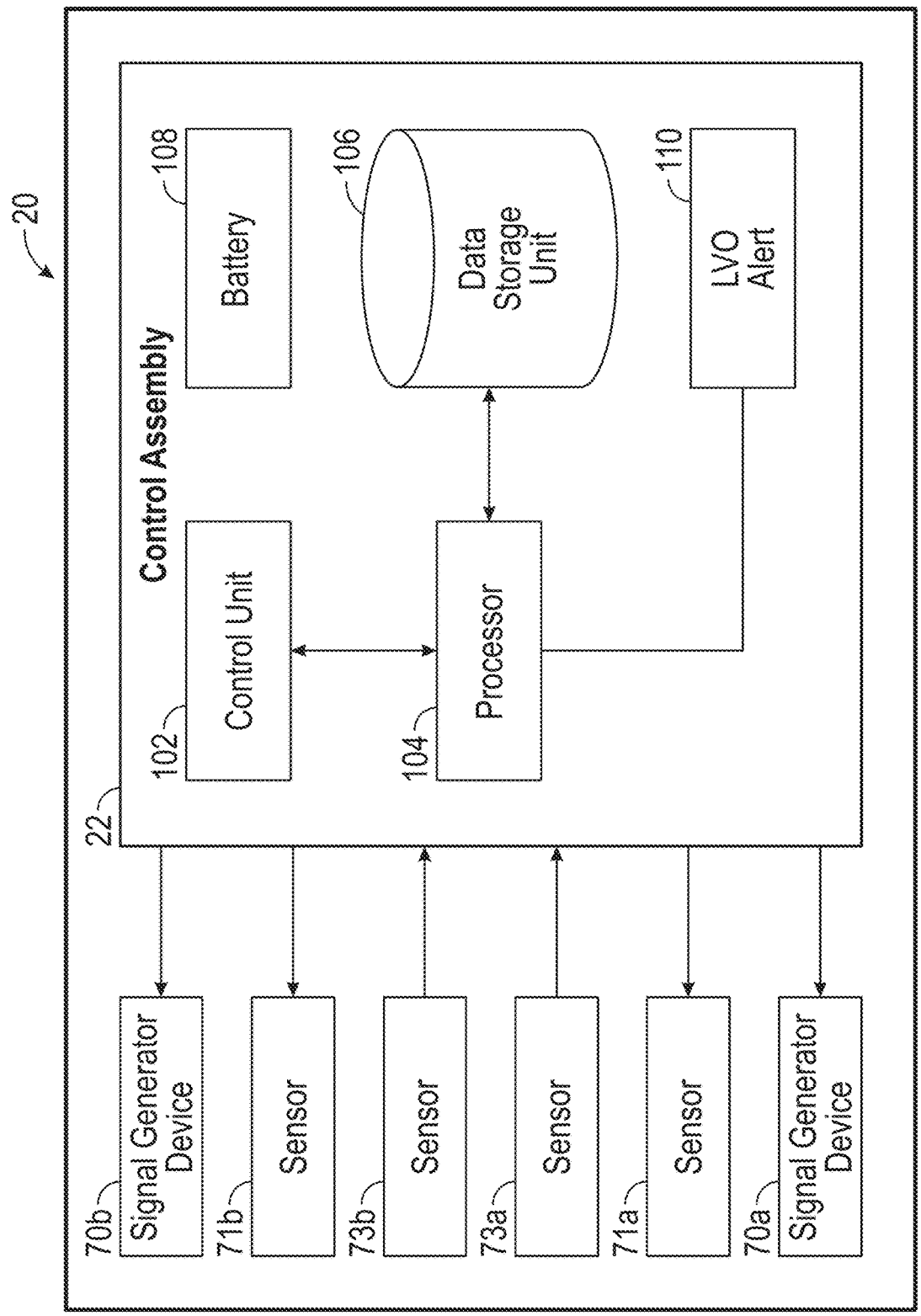
FIG. 4 is a block diagram illustrating a configuration of an exemplary control assembly of an embodiment of an LVO detector assembly of the present invention.

Referring to FIG. 4, in one embodiment, the control assembly 22 includes a control unit 102, a processor 104, a data storage unit 106 and a battery 108. Further, in this embodiment, each signal generation device 70*a*, 70*b*; sensors 71*a*, 71*b*, 73*a*, 73*b* and an LVO alert 110 communicate with the control assembly 22. In one embodiment, since the control assembly 22 is meant to be re-useable and to typically be deployed in harsh field conditions, the control assembly 22 is made to be rugged, rechargeable, reprogrammable and moisture-proof.

Figure 5:
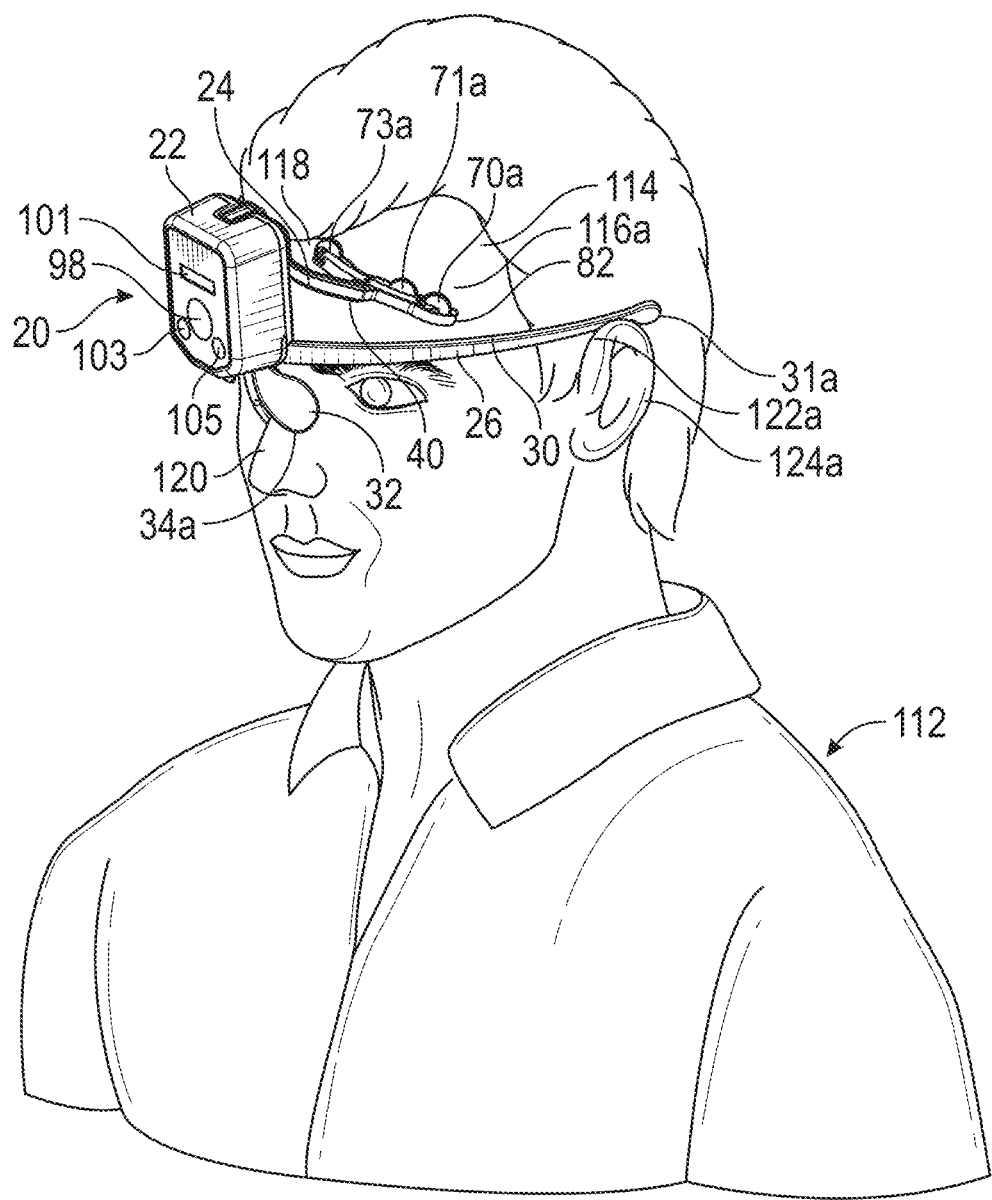
FIG. 5 is a front perspective view of an embodiment of an LVO detector assembly of the present invention situated on a patient's head.

Referring now to FIGS. 5-10, the operation of an embodiment of an LVO detection assembly 20 of the present invention is explained. When an LVO detection assembly user, such as a medical practitioner in the field (e.g., an EMT,) has a patient 112 that the user suspects of having an LVO and needs to do a quick assessment, the user retrieves an LVO detection assembly 20 for placement on the patient's head 114 (FIG. 5). If the LVO detection assembly 20 is a prefabricated, fully integrated device, the user can place the LVO detection assembly 20 directly on the patient's head 114 without assembly. If the LVO detection assembly 20 is in the separated component embodiment described above, the user may pre-assemble the LVO detection assembly 20 or assemble the LVO detection assembly 20 on the spot.

Since it is envisioned that the user may be assembling the components 22, 24, 26 on the spot in a rushed, emergency situation, features have been designed into an embodiment of the LVO detection assembly 20 to make it easier for the user to assemble the LVO detection assembly 20. Specifically, to assemble the LVO detection assembly 20, the user may pick up the sensor support structure 24 and line up the protruding connection piece 92 of the sensor support structure 24 with the top connection slot 96 of the control assembly 22. Once lined up, the user pushes the protruding connection piece 92 into the top connection slot 96. As the sensor support structure 24 is moved towards the control assembly 22, the power and control interface 80 of the sensor support structure 24 engages with, and forms an electrical connection with, the power and control interface 86 of the control assembly 22. In this embodiment, to assist with alignment of the power and control interfaces 80, 86, the embedded magnets 90*a*, 90*b* of the sensor support structure 24 attract to, and pair up with, a magnetically attracting portion of the control assembly 22. In addition, the alignment post 100 of the control assembly 22 engages with the alignment slot 94 of the sensor support structure 24. After connecting the sensor support structure 24 to the control assembly 22, the user connects the head engagement assembly 26 to the control assembly 22 by lining up the connection tab 99 of the head engagement assembly 26 with the bottom connection slot 97 of the control assembly 22.

Once lined up, the user pushes the connection tab 99 into the bottom connection slot 97. The LVO detector assembly 20 is now assembled and ready for use. It should be understood that the order in which the components 22, 24, 26 of the LVO detector assembly 20 are connected to one another is not important, and the components 22, 24, 26 may be connected to each other in any order.

With an LVO detector assembly 20 retrieved, the user places the LVO detector assembly 20 on the patient's head 114 as depicted in FIG. 5. To make the proper readings to determine if there is an LVO, it is important that the LVO detector assembly 20 be placed in a proper position on the patient's head 114, which includes being free from interference with hair. In a preferred embodiment, it has been found that the most reliable locations to place to the signal generation devices 70a, 70b and the sensors 71a, 71b, 73a, 73b to make proper readings is to place the signal generation devices 70a, 70b at or near the temples 116a, 116b (FIG. 9) of the patient 112; to place the sensors 71a, 71b towards the forehead 118 and adjacent the signal generation devices 70a, 70b; and to place the sensors 73a, 73b near the forehead 118 of the patient 112. This arrangement of the signal generation devices 70a, 70b to corresponding sensors 71a, 71b, 73a, 73b places the point of reflection generated by the LVO detector assembly 20 to be the Sylvian fissure, insular, and subinsular cortex adjacent to where the middle cerebral artery ("MCA") bifurcates. It has been found that this area is the location in the brain that is most sensitive to LVOs. Other systems have used large band of sensors to try to detect over the medial forehead in order to differentiate the anterior cerebral artery, superior M2 middle cerebral artery, and inferior M2 middle cerebral artery. It has been determined that detection of occlusions in those locations is unreliable, of little clinical value in the field and not representative of LVOs.

To help ensure that a user, even of limited experience or minimal training, places the LVO detector assembly 20 in the correct spot on the patient's head 114, the LVO detector assembly 20 of the present invention is designed so that no matter who is placing the LVO detector assembly 20 on the patient's head 114, the LVO detector assembly 20 will be put in the right place due to the relative invariability, no matter the patient 112, between the individual patient's relationship between the patient's nasal bridge 120, the root helices 122a, 122b of the ears 124a, 124b; the temples 116a, 166b and the forehead 118. No specialized training is required to place the LVO detector assembly 20 in the proper location, which was not the case with other LVO alert detection systems. Specifically, the user starts to slide the temple ends 31a, 31b over the patient's respective root helices 122a, 122b. As the user continues to slide LVO detection assembly 20 towards the back of the patient's head 114, over the root helices 122a, 122b, the signal generation devices 70a, 70b engage the temples 116a, 116b; the sensors 71a, 71b engage an area of the patient's head 114 between the forehead 118 and adjacent to the signal generation devices 70a, 70b; and the sensors 73a, 73b engage the patient's forehead 118. The hinged connectors 44a, 44b of the secondary support arms 42a, 42b; the hinged connectors 54, 56, 58, 60 of the component supports 46, 48, 50, 52 allow the signal generation devices 70a, 70b and the sensors 71a, 71b, 73a, 73b to move freely, as needed, to allow the LVO detector assembly 20 to form a proper, close fit on the patient's head 114, temples 116a, 116b and forehead 118. At the same time, the nose pads 34a, 34b of the nose support structure 32 engage the nasal bridge 120 of the patient 112. In this way, the LVO detector assembly 20 ensures it can reproducibly be placed on any patient relative to the areas of the forehead 118 and temples 116a, 116b over which the signal generation devices 70a, 70b and the sensors 71a, 71b 73a, 73b need to be placed to develop appropriate data to determine if the patient 112 is suffering from an LVO. In a preferred embodiment, when the LVO detector assembly 20 is in place on the patient's head 114, the signal generation devices 70a, 70b overlie the temples 116a, 116b and directly underneath both of which, at a depth of about 6 centimeters from the skin, lies the division of the MCA.

Figure 6:
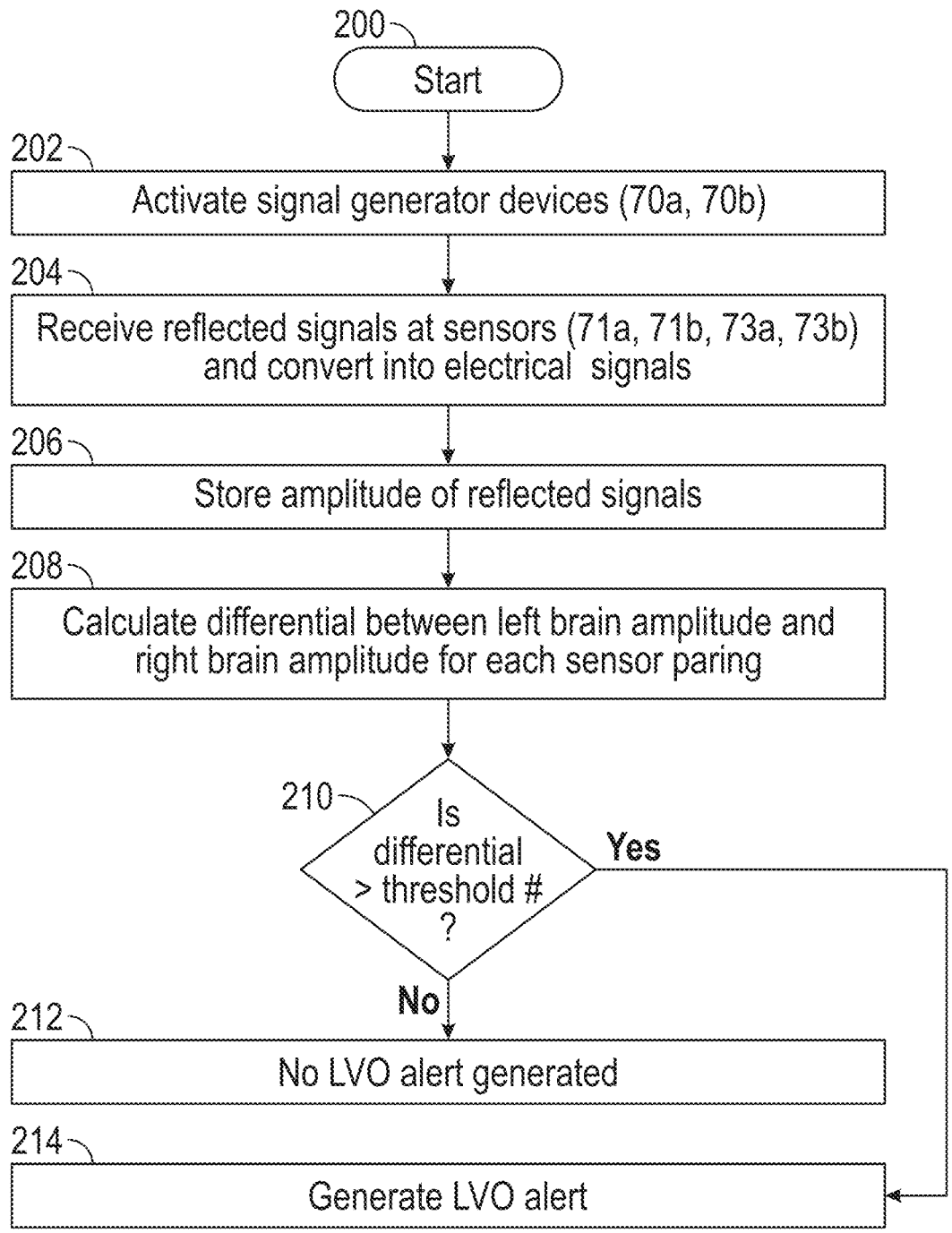
FIG. 6 is a flowchart illustrating the process of detecting an LVO with an embodiment of an LVO detector assembly of the present invention.
Figure 7:
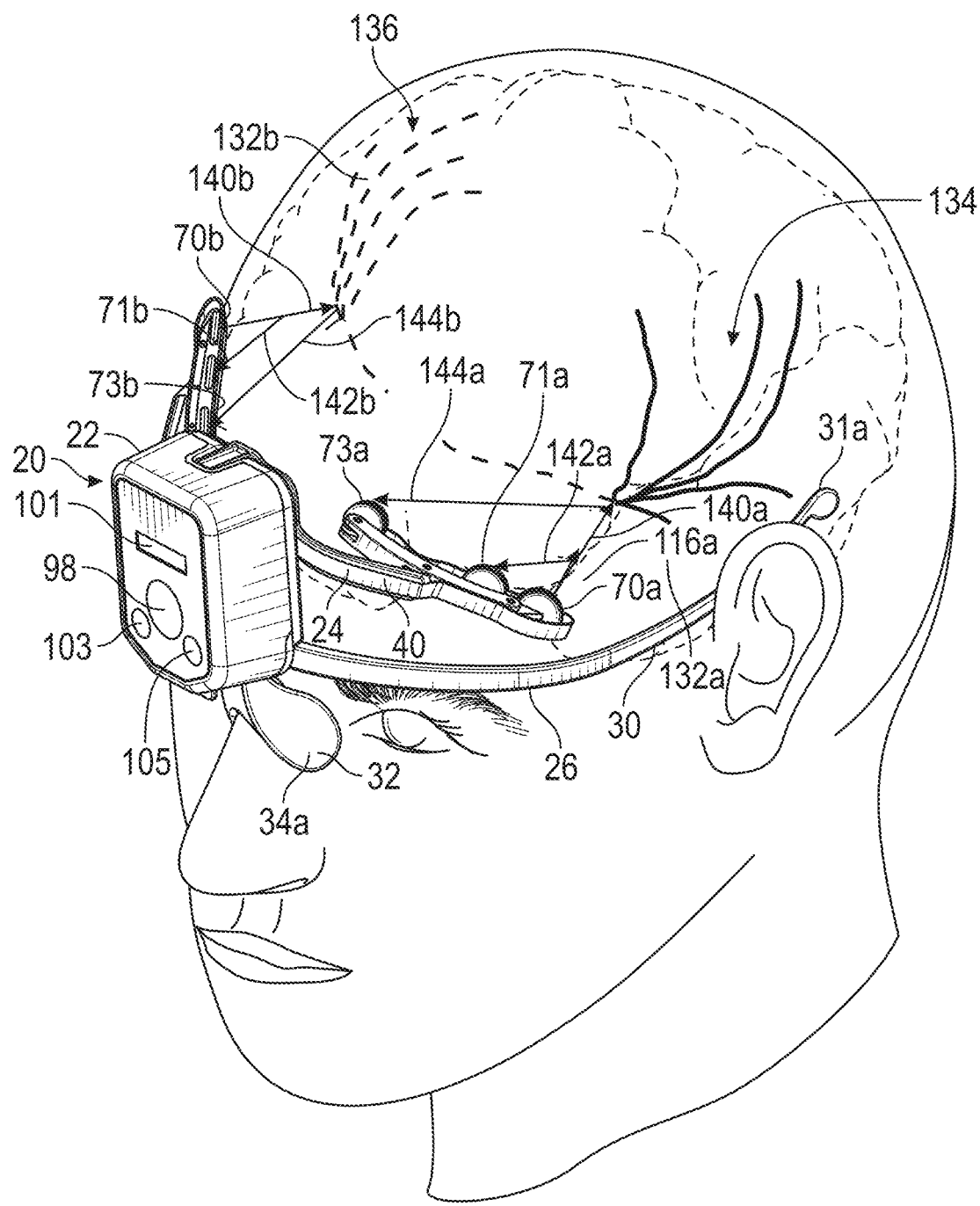
FIG. 7 is a front perspective view of an embodiment of an LVO detector assembly of the present invention situated on a patient's head, depicting an exemplary illustration of the transmission and reception of detection signals in the brain.
Figure 8:
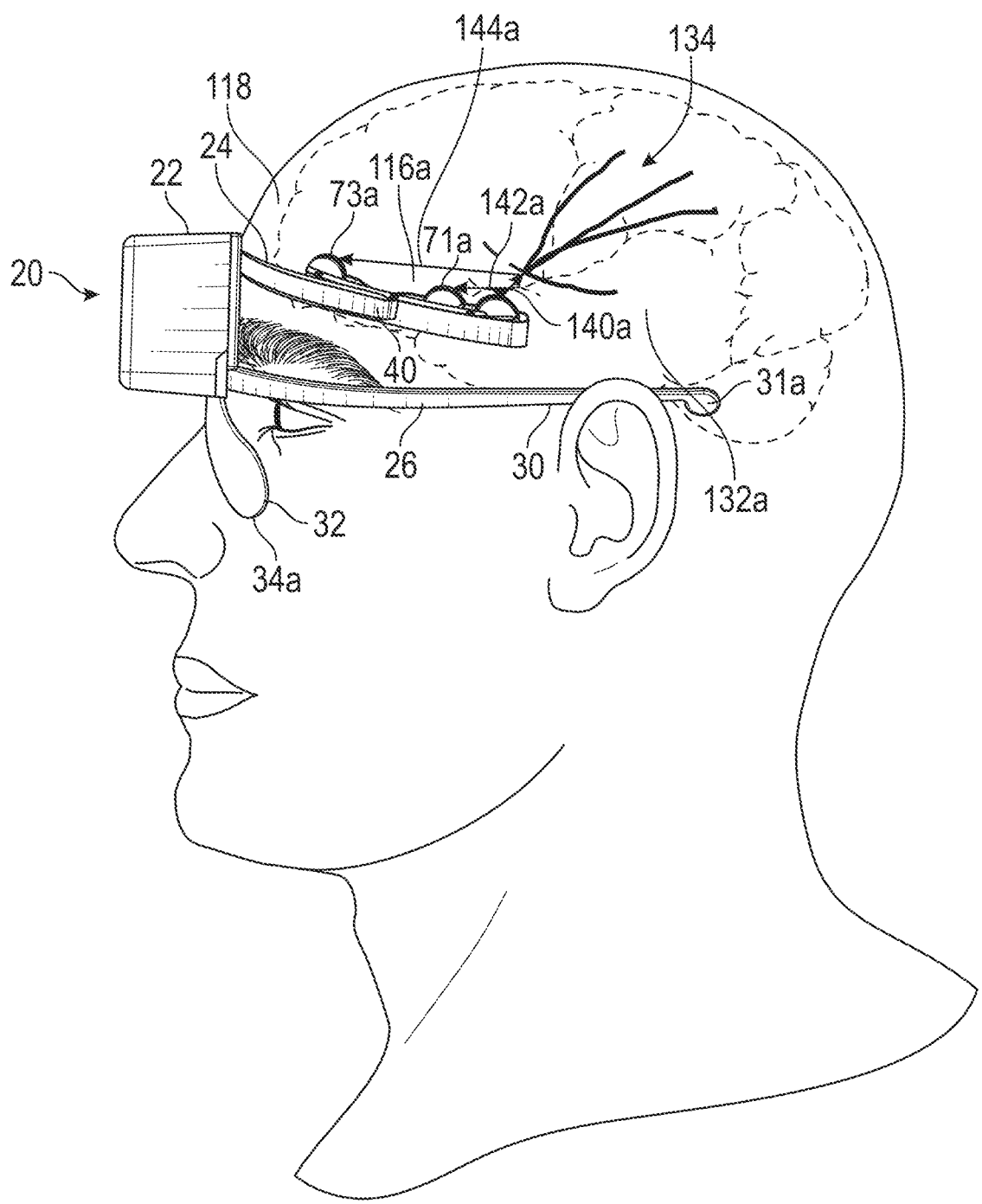
FIG. 8 is a side view of an embodiment of an LVO detector assembly of the present invention situated on a patient's head, depicting an exemplary illustration of the transmission and reception of detection signals in the brain.
Figure 9:
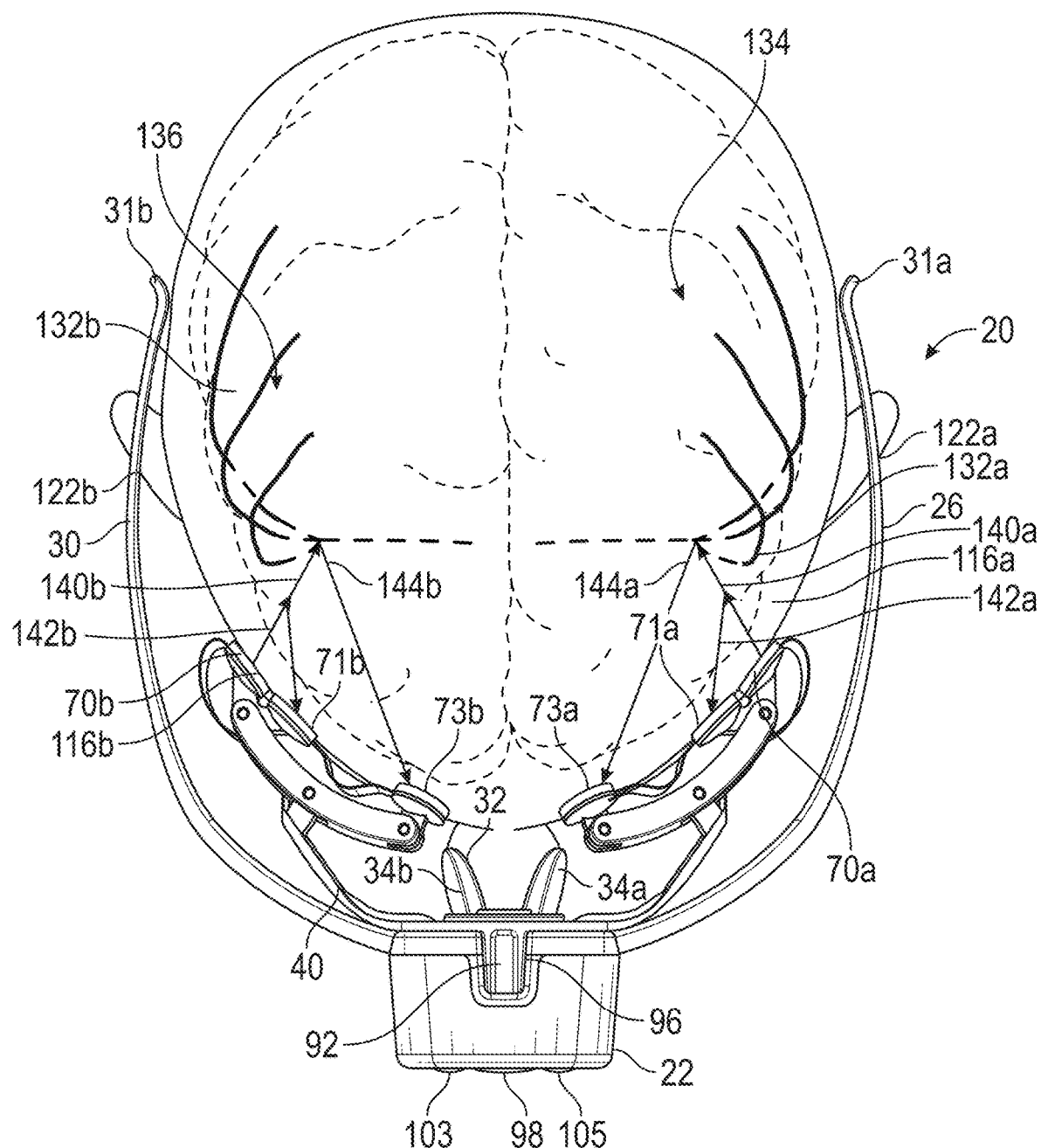
FIG. 9 is a top view of an embodiment of an LVO detector assembly of the present invention situated on a patient's head, depicting an exemplary illustration of the transmission and reception of detection signals in the brain.

With the LVO detector assembly 20 in place on the patient's head 114, the user now operates the LVO detector assembly 20. Referring now to FIG. 6, an embodiment of the process implemented by the control assembly 22 is depicted. The user turns on the LVO detector assembly 20 by pressing the power button 98 on the control assembly 22. When turned on, in this embodiment, the control unit 102, at step 202, activates the signal generation devices 70a, 70b to each transmit a single, reflective infrared or near-infrared signal 140a, 140b into each side of the patient's brain 132a, 132b (FIGS. 7-9). The transmitted signals 140a, 140b hit the matter of the brain 132a, 132b, in particular the blood vessel clusters 134, 136 on each side of the brain 132a, 132b. and reflect back towards the front portion of the head 114. At step 204, the sensors 71a, 71b, 73a, 73b receive infrared or near-infrared light 142a, 142b, 144a, 144b reflected back from the brain 132a, 132b. The reflected light 142a, 142b, received by sensors 71a, 71b, are shallow reflection data points of the present condition of their respective sides of the brain 132a, 132b, and the reflected light 144a, 144b, received by sensors 73a, 73b, are deeper reflection data points of the present condition of their respective sides of the brain 132a, 132b. The sensors 71a, 71b, 73a, 73b convert the received reflected light 142a, 142b, 144a, 144b into electrical signals, which represent the amplitude of each reflected signal. The process is collecting amplitude data for each reflected signal at a single point in time and is not measuring blood flow, over time, through the blood vessel clusters 134, 136. By not measuring blood flow, the present invention avoids the issue of patient variability in collateral blood flow recruitment in the LVO state and its effects on measuring blood flow to assess a blockage event. The process is doing a single reflection data point capture. The process then stores these single data point amplitudes in the data storage unit 106 (step 206). In this example, the amplitudes for signals 142a, 144a are measurements for the left side of the brain 132a, and the amplitudes for signals 142b, 144b are measurements for the right side of the brain 132b. At step 208, the process then calculates the amplitude differential between the data points for the left side and the right side of the brain 132a, 132b for each right and left side sensor pairing (i.e., the differential between the amplitude for signals 142a and 142b; the differential between the amplitude for signals 144a and 144b). In other embodiments, the process may also be collecting readings from the sensors 71a, 71b, 73a, 73b when the signal generation devices 70a, 70b are not transmitting signals 140a, 140b. Collecting this information allows the process to set a baseline for the sensors 71a, 71b, 73a, 73b to correct for ambient light noise. In embodiments implementing this methodology, before the process calculates the amplitude differential between the data points for the left side and the right side of the brain 132a, 132b for each right and left side sensor pairing at step 208, the process filters out the ambient light noise from the received signals 142a, 142b, 144a, 144b, using the data collected by the sensors 71a, 71b, 73a, 73b when the signal generation devices 70a, 70b were not transmitting signals 140a, 140b.

At step 210, the process compares each calculated left side-right side differential versus a threshold value stored in the data storage unit 106. If the calculated differential is less than the stored threshold value, the patient is not having an LVO incident, and no LVO alert is generated (Step 212). However, on the other hand, if the calculated differential is greater than the stored threshold value, the patient is having an LVO incident, and an LVO alert is generated (Step 214), which is displayed on the LVO alert screen 101; informing the user that he or she should send the patient 112 immediately to an EVT-capable hospital. The LVO detector assembly 20 of the present invention makes this determination using a single reflection datapoint capture and does not have to make multiple measurements to measure blood flow in the brain to make complex cerebral oximetry calculations.

Figure 10:
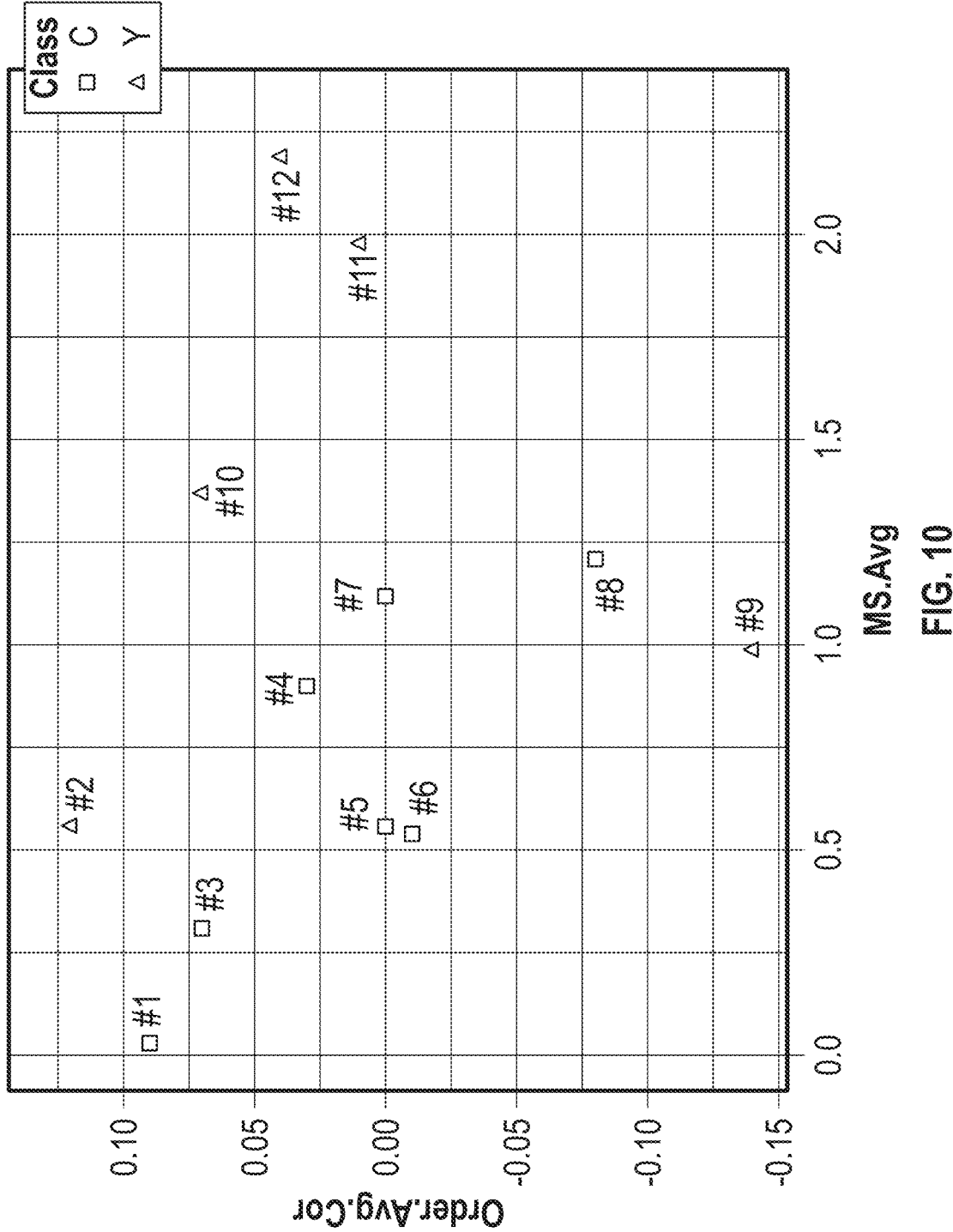
FIG. 10 is a graph illustrating two different exemplary ways to measure the similarity between a left and a right reflected shallow signal.

There are different ways to set a threshold and different ways to measure an amplitude difference against a threshold in differing embodiments of this invention. Referring now to FIG. 10, the figure depicts an exemplary way to measure the similarity between the left and right reflected shallow signals. A number of data points are shown for the calculations made for the right and left reflected shallow signals received. First, the signals discussed in these two embodiments are normalized by subtracting the average and representing each data point as the number of standard deviations from this mean (also called z-score normalization). The first way to measure the similarity between the left and right reflected shallow signals is depicted on the MS.Avg axis ("x-axis"). This axis shows the mean squared difference between the left and right amplitude values of the reflected shallow signals. This calculation captures the average separation of the left and right reflected shallow signals in intensity. Higher values mean the average intensity is more different between the two over any measured set of data. Another measure of similarity between the left and right reflected shallow signals is depicted on the Order. Avg.Cor axis ("y-axis"). This axis shows a rank order correlation between the left and right amplitude values of the reflected shallow signals. This value captures the degree to which the reflected shallow signals are similar. Zero means no correlation, a value of 1 means perfectly in synchrony, and −1 means perfectly out of synchrony.

Although certain embodiments and features of an LVO detector assembly have been described herein, the scope of coverage of this patent is not limited thereto. On the contrary, this patent covers all embodiments of the teachings of the disclosure that fairly fall within the scope of permissible equivalents.

What is claimed is:

1. A portable head-mounted diagnostic device for placing on a head of a patient for diagnosing conditions consistent with the existence of a blockage of a blood vessel in the brain of the patient, such as a large vessel occlusion, comprising:

a sensor support structure having a first signal generation device and at least one corresponding first reflected signal sensor located on one side of the sensor support structure and further having a second signal generation device and at least one corresponding second reflected signal sensor located on the opposite side of the sensor support structure, symmetric to the first signal generation device and to the at least one first reflected signal sensor;

a control assembly having an alert screen and storing a threshold value;

a head engagement assembly having a temple arm structure and a pair of nose supports;

wherein the sensor support structure, the control assembly and the head engagement assembly are connected to one another and the distance between the pair of nose supports, the temple arm and the sensor support structure is fixed such that when the portable head-mounted diagnostic device is placed on the head of the patient, the head engagement assembly places the first signal generation device and the at least one corresponding first reflected signal sensor in contact with the skin of the patient at approximately the temple area of the left side of the head of the patient, and places the second signal generation device and the at least one corresponding second reflected signal sensor in contact with the skin of the patient at approximately the temple area of the right side of the head of the patient; wherein the second signal generation device and the at least one corresponding second reflected signal sensor are in a position on the head of the patient that is symmetric to the first signal generation device and the at least one corresponding first reflected signal sensor that are in contact with the skin of the patient at approximately the temple area of the left side of the head of the patient;

wherein, in use, the first signal generation device transmits a single signal in a wavelength from a range of approximately 380 nanometers to 1 millimeter into the left side of the brain of the patient that hits a first blood vessel cluster, creating a first reflected signal on the left side of the brain and, concurrently, the second signal generation device transmits a single signal in a wavelength from a range of approximately 380 nanometers to 1 millimeter into the right side of the brain of the patient that hits a second blood vessel cluster, creating a second reflected signal on the right side of the brain;

wherein, in use, the at least one first reflected signal sensor receives the first reflected signal and the control assembly converts the received first reflected signal into a left side data point amplitude value, and the at least one second reflected signal sensor receives the second reflected signal and the control assembly converts the received second reflected signal into a right side data point amplitude value;

wherein the control assembly, using a single reflection datapoint capture of the first and second blood vessel clusters, calculates the difference between the left side data point amplitude value and the right side data point amplitude value and compares the calculated difference between the left side data point amplitude value and the right side data point amplitude value to the threshold value stored in the control assembly to determine if a large vessel occlusion condition exists, without the need to measure continuous blood flow in the first and second blood vessel clusters; and wherein when a large vessel occlusion exists, the control assembly generates an alert on the alert screen that a large vessel occlusion exists.

2. The portable head-mounted diagnostic device for placing on a head of a patient for diagnosing conditions consistent with the existence of a blockage of a blood vessel in the brain of a patient of claim 1, wherein the signal generation devices are light emitting diodes.

3. The portable head-mounted diagnostic device for placing on a head of a patient for diagnosing conditions consistent with the existence of a blockage of a blood vessel in the brain of a patient of claim 1, wherein the signal generation devices are infrared light emitting diodes.

4. The portable head-mounted diagnostic device for placing on a head of a patient for diagnosing conditions consistent with the existence of a blockage of a blood vessel in the brain of a patient of claim 1, wherein the signal generation devices are near infrared light emitting diodes.

5. The portable head-mounted diagnostic device for placing on a head of a patient for diagnosing conditions consistent with the existence of a blockage of a blood vessel in the brain of a patient of claim 1, wherein the temple arm structure sits on a root helix of the right ear and a root helix of the left ear.

6. The portable head-mounted diagnostic device for placing on a head of a patient for diagnosing conditions consistent with the existence of a blockage of a blood vessel in the brain of a patient of claim 1, wherein the sensor support structure is flexible and is configured to articulate to closely fit the head of the patient when placed on the patient, to snugly place the first signal generation device and the at least one corresponding first reflected signal sensor in contact with the skin of the patient at approximately the temple area of the left side of the head of the patient and to snugly place the second signal generation device and the at least one corresponding second reflected signal sensor in contact with the skin of the patient at approximately the temple area of the right side of the head of the patient.

7. The portable head-mounted diagnostic device for placing on a head of a patient for diagnosing conditions consistent with the existence of a blockage of a blood vessel in the brain of a patient of claim 1, wherein the control assembly; the sensor support structure and the head engagement assembly are separate components and are separable from one another.

8. The portable head-mounted diagnostic device for placing on a head of a patient for diagnosing conditions consistent with the existence of a blockage of a blood vessel in the brain of a patient of claim 7, wherein the sensor support structure and the head engagement assembly are disposable.

9. A portable head-mounted diagnostic device for placing on a head of a patient for diagnosing conditions consistent with the existence of a blockage of a blood vessel in the brain of the patient, such as a large vessel occlusion, comprising:
   a sensor support structure having a first signal generation device and a corresponding first shallow reflected signal sensor and a first deep reflected signal sensor located on one side of the sensor support structure and further having a second signal generation device and a corresponding second shallow reflected signal sensor and a second deep reflected signal sensor located on the opposite side of the sensor support structure, symmetric to the first signal generation device and the first shallow reflected signal sensor and the first deep reflected signal sensor;
   a control assembly having an alert screen and storing a threshold value;
   a head engagement assembly having a temple arm structure and a pair of nose supports;
   wherein the sensor support structure, the control assembly and the head engagement assembly are connected to one another and the distance between the pair of nose supports, the temple arm and the sensor support structure is fixed such that when the portable head-mounted diagnostic device is placed on the head of the patient, the head engagement assembly places the first signal generation device, the first shallow reflected signal sensor and the first deep reflected signal sensor in contact with the skin of the patient at approximately the temple area of the left side of the head of the patient, and places the second signal generation device, the second shallow reflected signal sensor and the second deep reflected signal sensor in contact with the skin of the patient at approximately the temple area of the right side of the head of the patient; wherein the second signal generation device, the second shallow reflected signal sensor and the second deep reflected signal sensor are in a position on the head of the patient that is symmetric to the first signal generation device, the first shallow reflected signal sensor and the first deep reflected signal sensor that are in contact with the skin of the patient at approximately the temple area of the left side of the head of the patient;
   wherein, in use, the first signal generation device transmits a single signal in a wavelength from a range of approximately 380 nanometers to 1 millimeter into the left side of the brain of the patient that hits a first blood vessel cluster, creating a first shallow reflected signal and a first deep reflected signal on the left side of the brain and, concurrently, the second signal generation device transmits a single signal in a wavelength from a range of approximately 380 nanometers to 1 millimeter into the right side of the brain of the patient that hits a second blood vessel cluster, creating a second shallow reflected signal and a second deep reflected signal on the right side of the brain;
   wherein, in use, the first shallow reflected signal sensor receives the first shallow reflected signal, the first deep reflected signal sensor receives the first deep reflected signal and the control assembly converts the received first shallow reflected signal and the received first deep reflected signal into a left side data point amplitude value, and the second shallow reflected signal sensor receives the second shallow reflected signal, the second deep reflected signal sensor receives the second deep reflected signal and the control assembly converts the received second shallow reflected signal and the received second deep reflected signal into a right side data point amplitude value;
   wherein the control assembly, using a single reflection datapoint capture of the first and second blood vessel clusters, calculates the difference between the left side data point amplitude value and the right side data point amplitude value and compares the calculated difference between the left side data point amplitude value and the right side data point amplitude value to the threshold value stored in the control assembly to determine if a large vessel occlusion condition exists, without the need to measure continuous blood flow in the first and second blood vessel clusters; and
   wherein when a large vessel occlusion exists, the control assembly generates an alert on the alert screen that a large vessel occlusion exists.

10. The portable head-mounted diagnostic device for placing on a head of a patient for diagnosing conditions consistent with the existence of a blockage of a blood vessel in the brain of a patient of claim 9, wherein the first shallow reflected signal sensor device is located between the right temple and a forehead of the patient and the second shallow reflected signal sensor device is located between the left temple and the forehead of the patient.

11. The portable head-mounted diagnostic device for placing on a head of a patient for diagnosing conditions consistent with the existence of a blockage of a blood vessel in the brain of a patient of claim 9, wherein the first deep reflected signal sensor device is located near a right side of a forehead of the patient and the second shallow reflected signal sensor device is located near a left side of the forehead of the patient.

12. The portable head-mounted diagnostic device for placing on a head of a patient for diagnosing conditions consistent with the existence of a blockage of a blood vessel in the brain of a patient of claim 9, wherein the signal generation devices are light emitting diodes.

13. The portable head-mounted diagnostic device for placing on a head of a patient for diagnosing conditions consistent with the existence of a blockage of a blood vessel in the brain of a patient of claim 9, wherein the signal generation devices are infrared light emitting diodes.

14. The portable head-mounted diagnostic device for placing on a head of a patient for diagnosing conditions consistent with the existence of a blockage of a blood vessel in the brain of a patient of claim 9, wherein the signal generation devices are near infrared light emitting diodes.

15. The portable head-mounted diagnostic device for placing on a head of a patient for diagnosing conditions consistent with the existence of a blockage of a blood vessel in the brain of a patient of claim 9, wherein the sensor support structure is flexible and is configured to articulate to closely fit the head of the patient when placed on the patient, to snugly place the first signal generation device, the first shallow reflected signal sensor and the first deep reflected signal sensor in contact with the skin of the patient at approximately the temple area of the left side of the head of the patient and to snugly place the second signal generation device, the second shallow reflected signal sensor and the second deep reflected signal sensor in contact with the skin of the patient at approximately the temple area of the right side of the head of the patient.

16. The portable head-mounted diagnostic device for placing on a head of a patient for diagnosing conditions consistent with the existence of a blockage of a blood vessel in the brain of a patient of claim 9, wherein the control assembly; the sensor support structure and the head engagement assembly are separate components and are separable from one another.

17. The portable head-mounted diagnostic device for placing on a head of a patient for diagnosing conditions consistent with the existence of a blockage of a blood vessel in the brain of a patient of claim 9, wherein the sensor support structure and the head engagement assembly are disposable.

18. A portable head-mounted diagnostic device for placing on a head of a patient for diagnosing conditions consistent with the existence of a blockage of a blood vessel in the brain of the patient, such as a large vessel occlusion, comprising:
  a sensor support structure having a first signal generation device and at least one corresponding first reflected signal sensor located on one side of the sensor support structure and further having a second signal generation device and at least one corresponding second reflected signal sensor located on the opposite side of the sensor support structure, symmetric to the first signal generation device and to the at least one first reflected signal sensor;
  a control assembly having an alert screen and storing a threshold value;
  a head engagement assembly having a temple arm structure and a pair of nose supports;
  wherein the sensor support structure, the control assembly and the head engagement assembly are connected to one another and the distance between the pair of nose supports, the temple arm and the sensor support structure is fixed such that when the portable head-mounted diagnostic device is placed on the head of the patient, the head engagement assembly places the first signal generation device and the at least one corresponding first reflected signal sensor in contact with a skin area on the left side of the head of the patient, and places the second signal generation device and the at least one corresponding second reflected signal sensor in contact with a skin area on the right side of the head of the patient; wherein the second signal generation device and the at least one corresponding second reflected signal sensor are in a position on the head of the patient that is symmetric to the first signal generation device and the at least one corresponding first reflected signal sensor that are in contact with the skin area on the left side of the head of the patient;
  wherein, in use, the first signal generation device transmits a single signal in a wavelength from a range of approximately 380 nanometers to 1 millimeter into the left side of the brain of the patient, which reflects approximately at a first blood vessel cluster where the middle cerebral artery bifurcates, creating a first reflected signal on the left side of the brain and, concurrently, the second signal generation device transmits a single signal in a wavelength from a range of approximately 380 nanometers to 1 millimeter into the right side of the brain of the patient, which reflects approximately at a second blood vessel cluster point where the middle cerebral artery bifurcates, creating a second reflected signal on the right side of the brain;
  wherein, in use, the at least one first reflected signal sensor receives the first reflected signal and converts the received first reflected signal into a left side data point amplitude value, and the at least one second reflected signal sensor receives the second reflected signal and converts the received second reflected signal into a right side data point amplitude value;
  wherein the control assembly calculates the difference between the left side data point amplitude value and the right side data point amplitude value and compares the calculated difference between the left side data point amplitude value and the right side data point amplitude value to the threshold value stored in the control assembly to determine if a large vessel occlusion condition exists without the need to measure continuous blood flow in the first and second blood vessel clusters; and
  wherein when a large vessel occlusion exists, the control assembly generates an alert on the alert screen that a large vessel occlusion exists.

19. The portable head-mounted diagnostic device for placing on a head of a patient for diagnosing conditions consistent with the existence of a blockage of a blood vessel in the brain of a patient of claim 18, wherein the signal generation devices are near infrared light emitting diodes.

20. The portable head-mounted diagnostic device for placing on a head of a patient for diagnosing conditions consistent with the existence of a blockage of a blood vessel in the brain of a patient of claim 18, wherein the control assembly; the sensor support structure and the head engagement assembly are separate components and are separable from one another.

* * * * *